US012797158B2

(12) United States Patent

Kopelman et al.

(10) Patent No.: US 12,797,158 B2

(45) Date of Patent: Nov. 17, 2026

(54) SELECTIVE IMAGE USE IN TOOTH MODEL GENERATION

(71) Applicant: Align Technology, Inc., San Jose, CA (US)

(72) Inventors: Avi Kopelman, Palo Alto, CA (US); Michael Sabina, Campbell, CA (US)

(73) Assignee: Align Technology, Inc., San Jose, CA (US)

( * ) Notice: Subject to any disclaimer, the term of this patent is extended or adjusted under 35 U.S.C. 154(b) by 204 days.

(21) Appl. No.: 18/778,840

(22) Filed: Jul. 19, 2024

(65) Prior Publication Data

US 2024/0366338 A1 Nov. 7, 2024

Related U.S. Application Data

(63) Continuation of application No. 18/141,292, filed on Apr. 28, 2023, now Pat. No. 12,070,367, which is a (Continued)

(51) Int. Cl.

| | |
|---|---|
| ***A61C 5/77*** | (2017.01) |
| ***A61B 1/00*** | (2006.01) |
| ***A61B 1/24*** | (2006.01) |
| ***A61C 9/00*** | (2006.01) |
| ***G06T 1/00*** | (2006.01) |
| ***G06T 7/13*** | (2017.01) |

(Continued)

(52) U.S. Cl.

CPC .............. *A61C 5/77* (2017.02); *A61B 1/0002* (2013.01); *A61B 1/00045* (2013.01); *A61B 1/24* (2013.01); *A61C 9/0053* (2013.01); *G06T 1/0007* (2013.01); *G06T 7/13* (2017.01); *G06T 15/205* (2013.01); *G06T 17/00* (2013.01); *A61B 1/000095* (2022.02); *G06T 2207/30036* (2013.01)

(58) Field of Classification Search

None

See application file for complete search history.

(56) References Cited

U.S. PATENT DOCUMENTS 6,075,905 A * 6/2000 Herman ................ G06T 3/4038 348/588

7,063,532 B1 6/2006 Jones et al.

(Continued)

FOREIGN PATENT DOCUMENTS

CN 101500503 A 8/2009

CN 101686853 A 3/2010

(Continued)

*Primary Examiner* — Nancy Bitar

(74) *Attorney, Agent, or Firm* — Lowenstein Sandler LLP

(57) ABSTRACT

A system comprises an intraoral scanner to generate intraoral images of a dental site, and a computing device. The computing device is configured to: receive an intraoral image comprising a depiction of a first tooth; determine a contour of the first tooth in the intraoral image; select a portion of the intraoral image that is within the contour of the first tooth; lock the portion of the intraoral image that is within the contour of the first tooth; and generate a 3D model comprising the first tooth and one or more other intraoral objects based at least in part on the intraoral image and one or more additional intraoral images, wherein the locked portion of the intraoral image is used for the first tooth in the 3D model.

20 Claims, 11 Drawing Sheets

Related U.S. Application Data continuation of application No. 16/810,726, filed on Mar. 5, 2020, now Pat. No. 11,678,953, which is a continuation of application No. 16/435,348, filed on Jun. 7, 2019, now Pat. No. 10,603,136, which is a continuation of application No. 15/993,504, filed on May 30, 2018, now Pat. No. 10,470,846, which is a continuation of application No. 15/222,525, filed on Jul. 28, 2016, now Pat. No. 10,004,572, which is a continuation of application No. 14/640,909, filed on Mar. 6, 2015, now Pat. No. 9,451,873.

(51) Int. Cl.

| | |
|---|---|
| ***G06T 15/20*** | (2011.01) |
| ***G06T 17/00*** | (2006.01) |

(56) References Cited

U.S. PATENT DOCUMENTS

| | | | | |
|---|---|---|---|---|
| 7,112,065 | B2 * | 9/2006 | Kopelman | A61C 13/0004 433/213 |
| 7,600,999 | B2 * | 10/2009 | Knopp | A61C 7/146 433/24 |
| D1,026,227 | S | 5/2024 | Ginzburg et al. | |
| 2009/0063273 | A1 * | 3/2009 | Dixon | G06Q 30/02 705/14.1 |
| 2013/0172731 | A1 | 7/2013 | Gole | |
| 2014/0172375 | A1 | 6/2014 | Grove et al. | |
| 2018/0028294 | A1 * | 2/2018 | Azernikov | G06K 9/6274 |

FOREIGN PATENT DOCUMENTS

| | | | |
|---|---|---|---|
| CN | 101969877 | A | 2/2011 |
| CN | 102741880 | A | 10/2012 |
| CN | 103648396 | A | 3/2014 |
| DE | 102010000451 | A1 | 8/2011 |
| JP | 2013537445 | A | 10/2013 |

* cited by examiner

SELECTIVE IMAGE USE IN TOOTH MODEL GENERATION

RELATED APPLICATIONS

The present application is a continuation of U.S. patent application Ser. No. 18/141,292, filed Apr. 28, 2023, which is a continuation of U.S. patent application Ser. No. 16/810,726, filed Mar. 5, 2020, now U.S. Pat. No. 11,678,953 issued Jun. 20, 2023, which is in turn a continuation of U.S. patent application Ser. No. 16/435,348, filed Jun. 7, 2019, now U.S. Pat. No. 10,603,136 issued Mar. 31, 2020, which is in turn a continuation of U.S. patent application Ser. No. 15/993,504, filed May 30, 2018, now U.S. Pat. No. 10,470,846 issued Nov. 12, 2019, which is in turn a continuation of U.S. patent application Ser. No. 15/222,525, filed Jul. 28, 2016, now U.S. Pat. No. 10,004,572 issued Jun. 26, 2018, which is in turn a continuation of U.S. patent application Ser. No. 14/640,909, filed Mar. 6, 2015, now U.S. Pat. No. 9,451,873 issued Sep. 27, 2016, all of which are incorporated by reference herein. The present application is also related to U.S. patent application Ser. No. 16/204,632, filed Nov. 29, 2018, now U.S. Pat. No. 10,219,875 issued Mar. 5, 2019.

TECHNICAL FIELD

Embodiments of the present invention relate to the field of intraoral scanning and, in particular, to a system and method for improving the results of intraoral scanning.

BACKGROUND

In prosthodontic procedures designed to implant a dental prosthesis in the oral cavity, the intraoral site at which the prosthesis is to be implanted in many cases should be measured accurately and studied carefully, so that a prosthesis such as a crown, denture or bridge, for example, can be properly designed and dimensioned to fit in place. A good fit enables mechanical stresses to be properly transmitted between the prosthesis and the jaw, and can prevent infection of the gums and tooth decay via the interface between the prosthesis and the intraoral site, for example. The intraoral site may be scanned to provide three-dimensional (3D) data of the intraoral site. However, if the area of a preparation tooth containing a finish line lacks definition, it may not be possible to properly determine the finish line, and thus the margin of a restoration may not be properly designed.

BRIEF DESCRIPTION OF THE DRAWINGS

The present invention is illustrated by way of example, and not by way of limitation, in the figures of the accompanying drawings.

DETAILED DESCRIPTION

Figure 1:
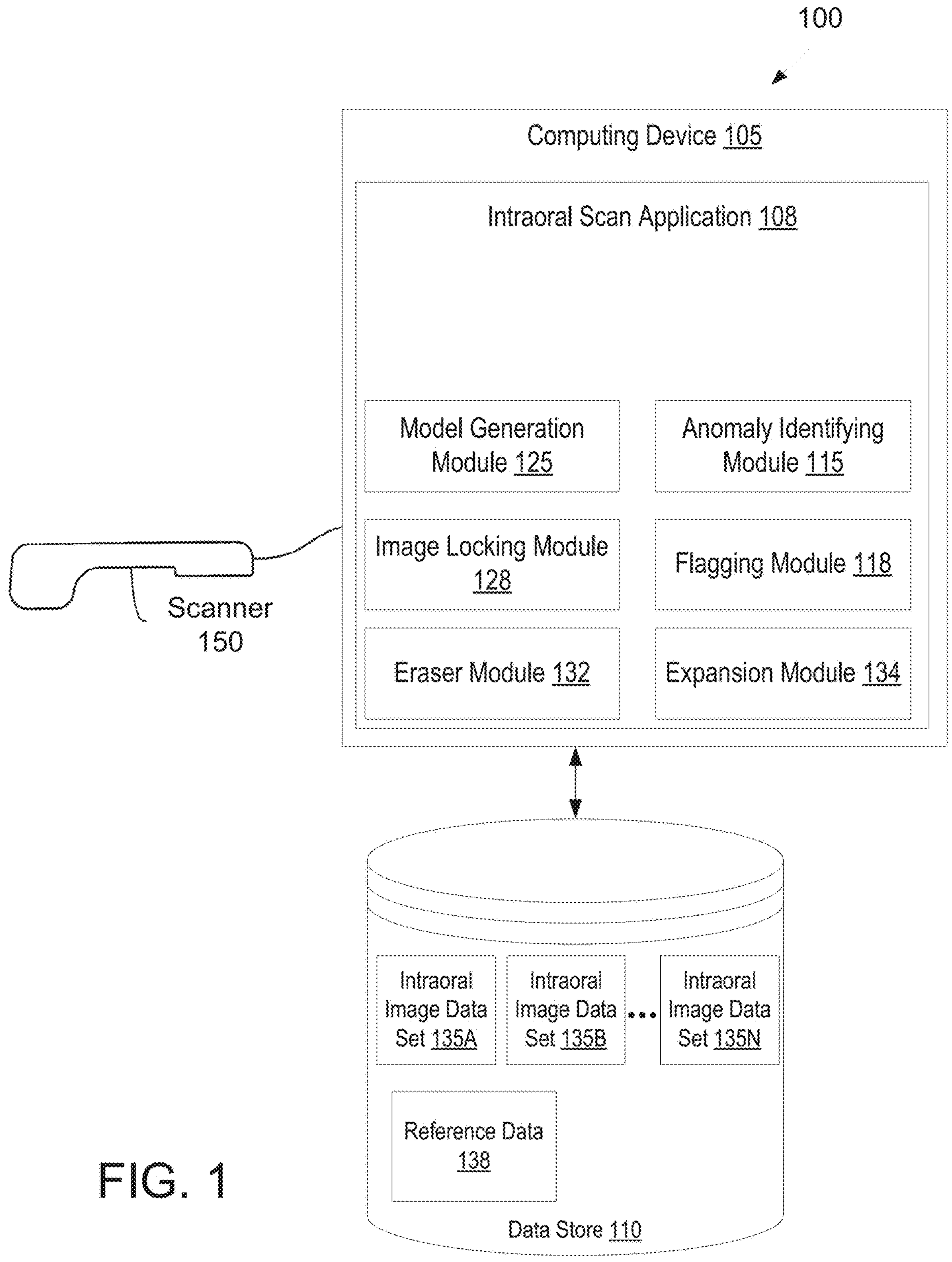
FIG. 1 illustrates one embodiment of a system for performing intraoral scanning and generating a virtual three-dimensional model of an intraoral site.

Described herein are a method and apparatus for improving the quality of scans, such as intraoral scans taken of intraoral sites (e.g., dental sites) for patients. During a scan session, a user (e.g., a dental practitioner) of a scanner may generate multiple different images (also referred to as scans) of an intraoral site, model of an intraoral site, or other object. The images may be discrete images (e.g., point-and-shoot images) or frames from a video (e.g., a continuous scan). The practitioner may take a first set of intraoral images of a first tooth after readying the first tooth for scanning. For example, if the first tooth is a preparation tooth (also referred to as a preparation), then one or more operations may be performed prior to generating the first set of intraoral images to ensure that a quality of the first set of intraoral images is high. In one example, these operations briefly expose a finish line of the preparation tooth to ensure that the finish line will show up in the first set of intraoral images.

After completing the first set of intraoral images, the practitioner may take additional sets of intraoral images of one or more adjacent teeth. The additional sets of intraoral images may include data for portions of the first tooth that was the focus of the first set of intraoral images. In some instances during creation of a 3D model using the intraoral images, the data from the additional sets of intraoral images combines with (e.g., is averaged with) the data for the first tooth from the first set of intraoral images to degrade a quality of that first tooth in the 3D model.

In embodiments, to prevent the data from the additional sets of intraoral images from degrading a quality of the first tooth in the 3D model, the first set of images is automatically locked after the first set of intraoral images is created. Additionally, portions of the first set of intraoral images that depict the first tooth may be exclusively used for the generation of the 3D model of that first tooth. Thus, the additional sets of intraoral images do not alter or add noise to a region of the 3D model depicting the first tooth as a result of the first set of intraoral image being locked. In one embodiment, an identity of the first tooth is determined, and the first portions of the first set of intraoral images are selected based at least in part on the identity of the first tooth. Thus, the lower quality data from the additional sets of intraoral images that depict the first tooth may not be applied when generating the 3D model of the first tooth. This may improve an image quality of the first tooth in the 3D model of an intraoral site (e.g., of a portion of a jaw).

Embodiments described herein are discussed with reference to intraoral scanners, intraoral images, intraoral scan sessions, and so forth. However, it should be understood that embodiments also apply to other types of scanners than intraoral scanners. Embodiments may apply to any type of scanner that takes multiple images and stitches these images together to form a combined image or virtual model. For example, embodiments may apply to desktop model scanners, computed tomography (CT) scanners, and so forth. Additionally, it should be understood that the intraoral scanners or other scanners may be used to scan objects other than intraoral sites in an oral cavity. For example, embodiments may apply to scans performed on physical models of an intraoral site or any other object. Accordingly, embodiments describing intraoral images should be understood as being generally applicable to any types of images generated by a scanner, embodiments describing intraoral scan sessions should be understood as being applicable to scan sessions for any type of object, and embodiments describing intraoral scanners should be understood as being generally applicable to many types of scanners.

FIG. 1 illustrates one embodiment of a system 100 for performing intraoral scanning and/or generating a virtual three-dimensional model of an intraoral site. In one embodiment, system 100 carries out one or more operations described below with reference to FIGS. 2-6.

System 100 includes a computing device 105 that may be coupled to a scanner 150 and/or a data store 110. Computing device 105 may include a processing device, memory, secondary storage, one or more input devices (e.g., such as a keyboard, mouse, tablet, and so on), one or more output devices (e.g., a display, a printer, etc.), and/or other hardware components. The computing device 105 may be integrated into the scanner 150 in some embodiments to improve performance and/or mobility.

Computing device 105 may be connected to data store 110 either directly or via a network. The network may be a local area network (LAN), a public wide area network (WAN) (e.g., the Internet), a private WAN (e.g., an intranet), or a combination thereof. Alternatively, data store 110 may be an internal data store. Examples of network data stores include a storage area network (SAN), a network attached storage (NAS), and a storage service provided by a cloud computing service provider. Data store 110 may include a file system, a database, or other data storage arrangement.

In some embodiments, a scanner 150 for obtaining three-dimensional (3D) data of an intraoral site in a patient's oral cavity is operatively connected to the computing device 105. Scanner 150 may include a probe (e.g., a hand held probe) for optically capturing three-dimensional structures (e.g., by confocal focusing of an array of light beams). One example of such a scanner 150 is the iTero® intraoral digital scanner manufactured by Align Technology, Inc. Other examples of intraoral scanners include the 3M™ True Definition Scanner and the Apollo DI intraoral scanner and CEREC AC intraoral scanner manufactured by Sirona®.

The scanner 150 may be used to perform an intraoral scan of a patient's oral cavity. An intraoral scan application 108 running on computing device 105 may communicate with the scanner 150 to effectuate the intraoral scan. A result of the intraoral scan may be one or more sets of intraoral images that have been discretely generated (e.g., by pressing on a "generate image" button of the scanner for each image). Alternatively, a result of the intraoral scan may be one or more videos of the patient's oral cavity. An operator may start recording the video with the scanner 150 at a first position in the oral cavity, move the scanner 150 within the oral cavity to a second position while the video is being taken, and then stop recording the video. The scanner 150 may transmit the discrete intraoral images or intraoral video (referred to collectively as intraoral image data sets 135A-135N) to the computing device 105. Computing device 105 may store the intraoral image data sets 135A-135N in data store 110. Alternatively, scanner 150 may be connected to another system that stores the intraoral image data sets 135A-135N in data store 110. In such an embodiment, scanner 150 may not be connected to computing device 105.

In one embodiment, intraoral scan application 108 includes an anomaly identifying module 115, a flagging module 118, a model generation module 125, an image locking module 128, an eraser module 132 and an expansion module 134. Alternatively, the operations of one or more of the anomaly identifying module 115, flagging module 118, model generation module 125, image locking module 128, eraser module 132 and/or expansion module 134 may be combined into a single module or separated into further modules.

According to an example, a user (e.g., a practitioner) may subject a patient to intraoral scanning. In doing so, the user may apply scanner 150 to one or more patient intraoral locations. The scanning may be divided into one or more segments. As an example, the segments may include a lower buccal region of the patient, a lower lingual region of the patient, a upper buccal region of the patient, an upper lingual region of the patient, one or more preparation teeth of the patient (e.g., teeth of the patient to which a dental device such as a crown or other dental prosthetic will be applied), one or more teeth which are contacts of preparation teeth (e.g., teeth not themselves subject to a dental device but which are located next to one or more such teeth or which interface with one or more such teeth upon mouth closure), and/or patient bite (e.g., scanning performed with closure of the patient's mouth with the scan being directed towards an interface area of the patient's upper and lower teeth). Via such scanner application, the scanner 150 may provide image data (also referred to as scan data) to computing device 105. The image data may be provided in the form of intraoral image data sets 135A-135N, each of which may include 2D intraoral images and/or 3D intraoral images of particular teeth and/or regions of an intraoral site. In one embodiment, separate image data sets are created for the maxillary arch, for the mandibular arch, for a patient bite, and for each preparation tooth. Such images may be provided from the scanner to the computing device 105 in the form of one or more points (e.g., one or more pixels and/or groups of pixels). For instance, the scanner 150 may provide such a 3D image as one or more point clouds.

The manner in which the oral cavity of a patient is to be scanned may depend on the procedure to be applied thereto. For example, if an upper or lower denture is to be created, then a full scan of the mandibular or maxillary edentulous arches may be performed. In contrast, if a bridge is to be created, then just a portion of a total arch may be scanned which includes an edentulous region, the neighboring preparation teeth (e.g., abutment teeth) and the opposing arch and dentition. Thus, the dental practitioner may input the identity of a procedure to be performed into intraoral scan application 108. For this purpose, the dental practitioner may choose the procedure from a number of preset options on a drop-down menu or the like, from icons or via any other suitable graphical user interface. Alternatively, the identity of the procedure may be input in any other suitable way, for example by means of preset code, notation or any other suitable manner, intraoral scan application 108 having been suitably programmed to recognize the choice made by the user.

By way of non-limiting example, dental procedures may be broadly divided into prosthodontic (restorative) and orthodontic procedures, and then further subdivided into specific forms of these procedures. Additionally, dental procedures may include identification and treatment of gum disease, sleep apnea, and intraoral conditions. The term prosthodontic procedure refers, inter alia, to any procedure involving the oral cavity and directed to the design, manufacture or installation of a dental prosthesis at a dental site within the oral cavity (intraoral site), or a real or virtual model thereof, or directed to the design and preparation of the intraoral site to receive such a prosthesis. A prosthesis may include any restoration such as crowns, veneers, inlays, onlays, implants and bridges, for example, and any other artificial partial or complete denture. The term orthodontic procedure refers, inter alia, to any procedure involving the oral cavity and directed to the design, manufacture or installation of orthodontic elements at a intraoral site within the oral cavity, or a real or virtual model thereof, or directed to the design and preparation of the intraoral site to receive such orthodontic elements. These elements may be appliances including but not limited to brackets and wires, retainers, clear aligners, or functional appliances.

For many prosthodontic procedures (e.g., to create a crown, bridge, veneer, etc.), an existing tooth of a patient is ground down to a stump. The ground tooth is referred to herein as a preparation tooth, or simply a preparation. The preparation tooth has a finish line (also referred to as a margin line), which is a border between a natural (unground) portion of the preparation tooth and the prepared (ground) portion of the preparation tooth. The preparation tooth is typically created so that a crown or other prosthesis can be mounted or seated on the preparation tooth. In many instances, the finish line of the preparation tooth is below the gum line. While the term preparation typically refers to the stump of a preparation tooth, including the finish line and shoulder that remains of the tooth, the term preparation herein also includes artificial stumps, pivots, cores and posts, or other devices that may be implanted in the intraoral cavity so as to receive a crown or other prosthesis. Embodiments described herein with reference to a preparation tooth also apply to other types of preparations, such as the aforementioned artificial stumps, pivots, and so on.

After the preparation tooth is created, a practitioner performs operations to ready that preparation tooth for scanning. Readying the preparation tooth for scanning may include wiping blood, saliva, etc. off of the preparation tooth and/or separating a patient's gum from the preparation tooth to expose the finish line. In some instances, a practitioner will insert a cord around the preparation tooth between the preparation tooth and the patient's gum. The practitioner will then remove the cord before generating a set of intraoral scans of the preparation tooth. The soft tissue of the gum will then revert back to its natural position, and in many cases collapses back over the finish line, after a brief time period. Accordingly, the practitioner uses the scanner 150 to scan the readied preparation tooth and generate a set of intraoral images (e.g., intraoral image data set 135A) of the preparation tooth before the soft tissue reverts back to its natural position.

After generating the set of intraoral images for the preparation tooth, the practitioner may preview the set of intraoral images (or a 3D model crated therefrom) to determine if the set of intraoral images have satisfactory quality. The practitioner may then either rescan the preparation tooth (or a portion thereof) if the quality is not satisfactory, or may proceed to generate additional sets of intraoral images (e.g., intraoral image sets 135B-135N) for adjacent teeth and other areas around the preparation tooth if the quality is satisfactory. These additional sets of intraoral images for the adjacent areas may be taken, for example, to ensure that a dental prosthesis will fit in the patient's mouth. The additional sets of intraoral images may also capture portions of the preparation tooth after the gum has collapsed back over the finish line and/or after blood and/or saliva has accumulated on the preparation tooth.

Accordingly, in one embodiment after a first set of intraoral images (e.g., intraoral image data set 135A) is taken (e.g., of a preparation tooth), image locking module 128 automatically locks that first set of intraoral images. The locked first set of intraoral images may be associated with a preparation tooth of a patient. In one embodiment, image locking module 128 automatically locks image data sets associated with preparation teeth, but does not automatically lock other image data sets. Accordingly, image locking module 128 may determine whether a new image data set is associated with a preparation tooth, and if so lock that image data set.

The identity of the preparation tooth may be used by image locking module 128 to automatically select portions of the locked first set of intraoral images that will be applied for the preparation tooth in a 3D model. Alternatively, a practitioner may use a graphical user interface (GUI) to mark the portions of the locked set of intraoral images that will be applied for the preparation tooth in the 3D model. In either case, the image locking module 128 may update the locked image data set so that only portions of the locked image data set that depict the preparation tooth are locked, while the portions of the image data set that depict gums, other teeth, etc. are unlocked. In one embodiment, image locking module 128 performs image processing to determine a contour of the preparation tooth as well as the finish line. All data representing the preparation tooth inside of the finish line may be locked, while all data representing other intraoral features outside of the finish line may be unlocked. In one embodiment, a buffer is applied, and all data within the finish line plus the buffer is locked. The buffer may be, for example, a 1-3 mm offset from the finish line. Thus, image locking module 128 may algorithmically determine what data to keep in the locked image data set. Alternatively, a user may manually determine what data to keep in the locked image data set. For example, the user may outline the area that he or she wishes to keep via the graphical user interface. This locked image data set can later be unlocked at any time by a user.

The data from additional sets of intraoral images, which may also include lower quality depictions of the preparation tooth, may be ignored by model generation module 125 during creation of the preparation tooth in the 3D model. Thus, the finish line captured in the first image data set is not degraded by further image data.

In a further embodiment, additional intraoral image data sets may be generated for additional preparation teeth and/or other teeth, such as teeth that are adjacent to a scanned preparation tooth. Image locking module 128 may automatically (e.g., algorithmically and/or without user input) lock some or all image data sets after the image data sets have been created and before additional intraoral images are taken. Image locking module 128 may assign each locked intraoral image data set 135A-135N a separate layer or group identifier. These layers may be used to refer to entire image data sets, and may be used to display or hide image data sets and/or to prioritize data from image data sets for stitching together such image data sets.

In an example, a first image data set may be associated with a first tooth and a second image data set may be associated with an adjacent second tooth. Data from the first image data set may overlap data from the second image data set, and may diverge from the data from the second image data set. To stitch together the image data sets, the discrepancies between overlapping regions of an intraoral site depicted in these two image data sets should be remedied. One technique of remedying the discrepancies is to average the data of the first image data set with the data of the second image data set for the overlapping regions. With the use of layers, a weight may be assigned to each image data set, and the averaging of the image data sets may be a weighted average. For example, if a user knows that data for a particular overlapping region from a first image data set is superior in quality to data for the particular overlapping region of the second image data set, the user may select the first image data set as having a higher priority. Model generation module 125 may then weight the first image data set more heavily than the second image data set when averaging the differences between the image data sets.

Image locking module 128 may associate each intraoral image data set 135A-135N with a particular tooth and/or may otherwise identify an intraoral site associated with each intraoral image data set 135A-135N. In one embodiment, a user indicates which tooth he or she is scanning before generating an image data set. Alternatively, a user may first take an image data set, and may subsequently indicate a tooth imaged in the image data set. In another implementation, intraoral scan application 108 may instruct the user to scan a particular tooth, and may associate an identity of that particular tooth with the image data set. Thus, each locked intraoral image data set 135A-135N may be associated with a particular tooth, which may or may not be a preparation tooth.

When a scan session is complete (e.g., all images for an intraoral site have been captured), model generation module 125 may generate a virtual 3D model of the scanned intraoral site. To generate the virtual 3D model, model generation module 125 may register (i.e., "stitch" together) the intraoral images generated from the intraoral scan session. In one embodiment, performing image registration includes capturing 3D data of various points of a surface in multiple images (views from a camera), and registering the images by computing transformations between the images. The images may then be integrated into a common reference frame by applying appropriate transformations to points of each registered image.

In one embodiment, image registration is performed for each pair of adjacent or overlapping intraoral images (e.g., each successive frame of an intraoral video). Image registration algorithms are carried out to register two adjacent intraoral images, which essentially involves determination of the transformations which align one image with the other. Image registration may involve identifying multiple points in each image (e.g., point clouds) of an image pair, surface fitting to the points of each image, and using local searches around points to match points of the two adjacent images. For example, model generation module 125 may match points of one image with the closest points interpolated on the surface of the other image, and iteratively minimize the distance between matched points. Model generation module 125 may also find the best match of curvature features at points of one image with curvature features at points interpolated on the surface of the other image, without iteration. Model generation module 125 may also find the best match of spin-image point features at points of one image with spin-image point features at points interpolated on the surface of the other image, without iteration. Other techniques that may be used for image registration include those based on determining point-to-point correspondences using other features and minimization of point-to-surface distances, for example. Other image registration techniques may also be used.

Many image registration algorithms perform the fitting of a surface to the points in adjacent images, which can be done in numerous ways. Parametric surfaces such as Bezier and B-Spline surfaces are most common, although others may be used. A single surface patch may be fit to all points of an image, or alternatively, separate surface patches may be fit to any number of a subset of points of the image. Separate surface patches may be fit to have common boundaries or they may be fit to overlap. Surfaces or surface patches may be fit to interpolate multiple points by using a control-point net having the same number of points as a grid of points being fit, or the surface may approximate the points by using a control-point net which has fewer number of control points than the grid of points being fit. Various matching techniques may also be employed by the image registration algorithms.

In one embodiment, model generation module 125 may determine a point match between images, which may take the form of a two dimensional (2D) curvature array. A local search for a matching point feature in a corresponding surface patch of an adjacent image may be carried out by computing features at points sampled in a region surrounding the parametrically similar point. Once corresponding point sets are determined between surface patches of the two images, determination of the transformation between the two sets of corresponding points in two coordinate frames can be solved. Essentially, an image registration algorithm may compute a transformation between two adjacent images that will minimize the distances between points on one surface, and the closest points to them found in the interpolated region on the other image surface used as a reference.

Model generation module 125 repeats image registration for all adjacent image pairs of a sequence of intraoral images to obtain a transformation between each pair of images, to register each image with the previous one. Model generation module 125 then integrates all images into a single virtual 3D model by applying the appropriate determined transformations to each of the images. Each transformation may include rotations about one to three axes and translations within one to three planes.

In many instances, data from one set of intraoral images does not perfectly correspond to data from another set of intraoral images. For each intraoral image data set 135A-135N, image locking module 128 may use the identity of the associated tooth to determine what portions of that image data set will be used exclusively for creation of a particular region of a 3D model (e.g., for creation of the associated tooth in the 3D model). The image locking module 128 may analyze the image data in each intraoral image data set. For each image data set, the image locking module 128 may use stored information about an associated tooth to determine from the analysis which portions or areas of that image data set represent that tooth and which portions or areas of that image data set represent other intraoral objects such as gums and other teeth. The selection module 130 may then generate a contour of that tooth in the image data set. The generated contour may act as a border. Data from the image data set that is within the contour may be exclusively used by model generation module 125 to generate the specific associated tooth in a 3D model. Data from the image data set that is outside of the contour may or may not be used to generate additional features or objects in the 3D model. Additionally, data outside the contour may be combined with data from other image data sets to generate the additional features or objects in the 3D model.

In one embodiment, the operation of contouring the tooth in a locked image data set is performed by image locking module (as described above). Image locking module 128 may then update the locked image data set to lock portions of the image data set inside of the contour and unlock portions of the image data set outside of the contour.

Anomaly identifying module 115 is responsible for identifying anomalies and/or other areas of interest (AOIs) from intraoral scan data (e.g., intraoral images in an intraoral image data set) and/or virtual 3D models generated from intraoral scan data. Such anomalies may include voids (e.g., areas for which scan data is missing), areas of conflict or flawed scan data (e.g., areas for which overlapping surfaces of multiple intraoral images fail to match), areas indicative of foreign objects (e.g., studs, bridges, etc.), unclear margin line (e.g., margin line of one or more preparation teeth), noisy information, and so forth. An identified void may be a void in a surface of an image. Examples of surface conflict include double incisor edge and/or other physiologically unlikely tooth edge, bite line shift, inclusion or lack of blood, saliva and/or foreign objects, differences in depictions of a margin line, and so on. The anomaly identifying module 115 may, in identifying an anomaly, analyze patient image data (e.g., 3D image point clouds) and/or one or more virtual 3D models of the patient alone and/or relative to reference data 138. The analysis may involve direct analysis (e.g., pixel-based and/or other point-based analysis), the application of machine learning, and/or the application of image recognition. Such reference data 138 may include past data regarding the at-hand patient (e.g., intraoral images and/or virtual 3D models), pooled patient data, and/or pedagogical patient data, some or all of which may be stored in data store 110.

Anomaly identifying module 115 to identify anomalies by performing image processing to identify an unexpected shape, a region with low clarity, a region missing data, color discrepancies, and so forth. Different criteria may be used to identify different classes of anomalies. In one embodiment, an area of missing image data is used to identify anomalies that might be voids. For example, voxels at areas that were not captured by the intraoral images may be identified. In one embodiment, anomaly identifying module interpolates a shape for the anomaly based on geometric features surrounding the anomaly and/or based on geometric features of the anomaly (if such features exist). Such geometric features may be determined by using edge detection, corner detection, blob detection, ridge detection, Hough transformations, structure tensors, and/or other image processing techniques.

The data regarding the at-hand patient may include X-rays, 2D intraoral images, 3D intraoral images, 2D models, and/or virtual 3D models corresponding to the patient visit during which the scanning occurs. The data regarding the at-hand patient may additionally include past X-rays, 2D intraoral images, 3D intraoral images, 2D models, and/or virtual 3D models of the patient (e.g., corresponding to past visits of the patient and/or to dental records of the patient).

The pooled patient data may include X-rays, 2D intraoral images, 3D intraoral images, 2D models, and/or virtual 3D models regarding a multitude of patients. Such a multitude of patients may or may not include the at-hand patient. The pooled patient data may be anonymized and/or employed in compliance with regional medical record privacy regulations (e.g., the Health Insurance Portability and Accountability Act (HIPAA)). The pooled patient data may include data corresponding to scanning of the sort discussed herein and/or other data. The pedagogical patient data may include X-rays, 2D intraoral images, 3D intraoral images, 2D models, virtual 3D models, and/or medical illustrations (e.g., medical illustration drawings and/or other images) employed in educational contexts. The pedagogical patient data may include volunteer data and/or cadaveric data.

Anomaly identifying module 115 may analyze patient scan data from later in a patient visit during which the scanning occurs (e.g., one or more later-in-the-visit 3D image point clouds and/or one or more later-in-the-visit virtual 3D models of the patient) relative to additional patient scan data in the form of data from earlier in that patient visit (e.g., one or more earlier-in-the-visit 3D image point clouds and/or one or more earlier-in-the-visit virtual 3D models of the patient). Anomaly identifying module 115 may additionally or alternatively analyze patient scan data relative to reference data in the form of dental record data of the patient and/or data of the patient from prior to the patient visit (e.g., one or more prior-to-the-visit 3D image point clouds and/or one or more prior-to-the-visit virtual 3D models of the patient). Anomaly identifying module 115 may additionally or alternatively analyze patient scan data relative to pooled patient data and/or pedagogical patient data.

Identifying of anomalies concerning missing and/or flawed scan data may involve the anomaly identifying module 115 performing direct analysis, for instance determining one or more pixels or other points to be missing from patient scan data and/or one or more virtual 3D models of the patient. Identification of anomalies concerning missing and/or flawed scan data may additionally or alternatively involve employing pooled patient data and/or pedagogical patient data to ascertain patient scan data and/or virtual 3D models as being incomplete (e.g., possessing discontinuities) relative to that which is indicated by the pooled patient data and/or pedagogical patient data.

Flagging module 118 is responsible for determining how to present and/or call out the identified anomalies. Flagging module 118 may provide indications or indicators of anomalies. The indications may be presented (e.g., via a user interface) to a user (e.g., a practitioner) in connection with and/or apart from one or more depictions of teeth and/or gingivae of a patient (e.g., in connection with one or more X-rays, 2D intraoral images, 3D intraoral images, 2D models, and/or virtual 3D models of the patient). Indication presentation in connection with depictions of patient teeth and/or gingivae may involve the indications being placed so as to correlate an indication with the corresponding portion of the teeth and/or gingivae.

The indications may be provided in the form of flags, markings, contours, text, images, and/or sounds (e.g., in the form of speech). Such a contour may be placed (e.g., via contour fitting) so as to follow an extant tooth contour and/or gingival contour (e.g., as a border). As an illustration, a contour corresponding to a void may be placed so as to follow a contour of the missing data. Such a contour may be placed (e.g., via contour extrapolation) with respect to a missing tooth contour and/or gingival contour so as to follow a projected path of the missing contour. As an illustration, a contour corresponding to missing tooth scan data may be placed so as to follow the projected path of the tooth portion which is missing, or a contour corresponding to missing gingival scan data may be placed so as to follow the projected path of the gingival portion which is missing.

Data for portions of the intraoral image data set that is within the contoured anomaly may be unlocked or removed from the locked intraoral image data set. The anomaly may be identified to a user, and the user may then generate a new intraoral image that captures the area of the anomaly in the intraoral site. The portion of the new intraoral image that corresponds to an inside of the contour of the anomaly is then used to replace the original data from the intraoral image data set for the anomaly. This data may then be added to the locked image data set. Thus, anomalies may be automatically detected in a set of intraoral images, and an additional intraoral image may be taken to overwrite the anomaly without affecting the rest of the intraoral image data set.

In one embodiment, after anomaly identifying module 115 identifies an anomaly, anomaly identifying module 115 may then determine whether there are any additional image data sets that include data covering the area at which the anomaly was identified. Anomaly identifying module 115 may compare this area from the one or more additional image data sets to the data of the locked image data set. Based on this comparison, anomaly identifying module 115 may determine that the data of the locked image data set covering the contour is to be replaced by data from another image data set. The portion of the other image data set that corresponds to an inside of the contour of the anomaly may then be used to replace the original data from the intraoral image data set for the anomaly. This data may then be added to the locked image data set.

In one embodiment, a different replacement option is presented to a user for each additional image data set. Thus, for each additional image data set, anomaly identifying module 115 may replace the anomaly with image data covering the contour of the anomaly from that additional image data set. Each of the replacement options may be presented to the user, who may then select which of the replacement options to apply. Once a user selection has been received, the data from the additional image data set associated with the user selection may be used to replace the anomaly in the locked image data set.

A 3D model created by model generation module 125 may be displayed to a user via a user interface of intraoral scan application. The 3D model can then be checked visually by the user. The user can virtually manipulate the 3D model via the user interface with respect to up to six degrees of freedom (i.e., translated and/or rotated with respect to one or more of three mutually orthogonal axes) using suitable user controls (hardware and/or virtual) to enable viewing of the 3D model from any desired direction. In addition to anomaly identifying module 115 algorithmically identifying anomalies for rescan, a user may review (e.g., visually inspect) the generated 3D model of an intraoral site and determine that one or more areas of the 3D model are unacceptable.

Based on the inspection, the user may determine that part of the 3D model is unsuitable or undesired, and that a remainder of the 3D model is acceptable. The unacceptable portion of the 3D model can correspond, for example, to a part of a real dental surface of a scanned intraoral site that was not sufficiently clearly defined in the 3D model. For example, during the initial 3D data collection step, for example via scanning, that resulted in the first 3D virtual model being generated, the corresponding part of the physical dental surface may have been covered with foreign material, such as for example saliva, blood, or debris. The corresponding part of the physical dental surface may also have been obscured by another element such as for example part of the gums, cheek, tongue, dental instruments, artifacts, etc. Alternatively, for example, during the initial 3D data collection step (e.g., via scanning) that resulted in the first 3D virtual model being generated, the unacceptable portion may be distorted or otherwise defective and may not properly correspond to a physical dental surface (e.g., due to some defect in the actual scanning process).

Via the user interface, a user may mark or otherwise demarcate the unacceptable portion of the 3D model. Eraser module 132 may then delete or otherwise remove the marked portion from the 3D model (and the associated portions of a locked image data set and/or other image data set used to create the unacceptable portion). For example, the dental procedure of interest may be providing a dental prosthesis, and the deleted or removed part of the 3D model may be part of a finish line of a tooth preparation that exists in a real dental surface, but was not clearly represented in the 3D model (or in the intraoral image data sets 135A-135N used to create the 3D model).

Intraoral scan application 108 may direct a user to generate one or more additional intraoral images of the dental site corresponding to the portion of the 3D model (and corresponding set or sets of intraoral images) that was deleted or removed. The user may then use the scanner 150 to generate the one or more additional intraoral images, which at least partially overlaps with previously generated intraoral images. The one or more additional intraoral images may be registered with the 3D model (and/or with the intraoral image data sets used to create the 3D model) to provide a composite of the 3D model and the one or more additional intraoral images. In the composite, the part of the 3D model that was previously deleted/removed is at least partially replaced with a corresponding part of the one or more additional intraoral images. However, the portions of the one or more additional images that are outside of the deleted or removed part of the 3D model are not applied to the composite or updated 3D model. In one embodiment, the portion of the new intraoral image that corresponds to the erased portion of a locked image data set is added to the locked image data set.

Expansion module 134 may perform operations similar to those of anomaly identifying module 115 and/or eraser module 132. However, rather than identifying and correcting anomalies or unacceptable portions within a 3D model, expansion module 134 may identify and/or correct portions of the 3D model at an edge of the 3D model. For example, an intraoral image data set 135A may have missed a portion of a tooth such that the tooth is cut off in the 3D model (e.g., a portion of the tooth is not shown in the 3D model). Expansion module 134 may algorithmically detect an edge of the 3D model where a tooth appears to be clipped.

Alternatively, a user may indicate via the user interface that a portion of the tooth is not represented in the 3D model. The user may or may not mark a portion of edge of the 3D model where the model is incomplete.

A user may then use scanner 150 to generate one or more additional intraoral images of the intraoral site (e.g., tooth) corresponding to the area of the 3D model where data was missing. The one or more additional intraoral images may be registered to the 3D model. Expansion module 134 may then determine that a portion of the one or more additional intraoral images represents a region of the intraoral site (e.g., tooth) that was missing from the initial 3D model. This portion of the one or more additional intraoral images may then be added to the 3D model to expand the 3D model for the intraoral site (e.g., tooth). Additionally, the portion of the one or more additional intraoral images may be appended to a locked image data set.

In one embodiment, a practitioner may have generated a full or partial scan of one or more dental arches of a patient. At some time after the scan was completed, the patient may experience a change in dental health, and may require a bridge or other prosthodontic to be applied where there used to be a health tooth. In such an instance, the dental practitioner may leverage the previously completed scan. In particular, the practitioner may generate a preparation tooth, and may then scan that preparation tooth to generate a locked intraoral image data set of the preparation tooth. This locked intraoral image data set may then be combined with the previously generated scan data to create a new 3D model of the patient's dental arch. Most of the arch in the new 3D model will be based on data from the original scan, while the data for the preparation tooth will be based on the locked image data set.

FIGS. 2-6 illustrate flow diagrams for methods of processing sets of intraoral images and generating virtual 3D models therefrom. These methods may be performed by processing logic that comprises hardware (e.g., circuitry, dedicated logic, programmable logic, microcode, etc.), software (such as instructions run on a processing device), or a combination thereof. In one embodiment, processing logic corresponds to computing device 105 of FIG. 1 (e.g., to a computing device 105 executing an intraoral scan application 108).

Figure 2:
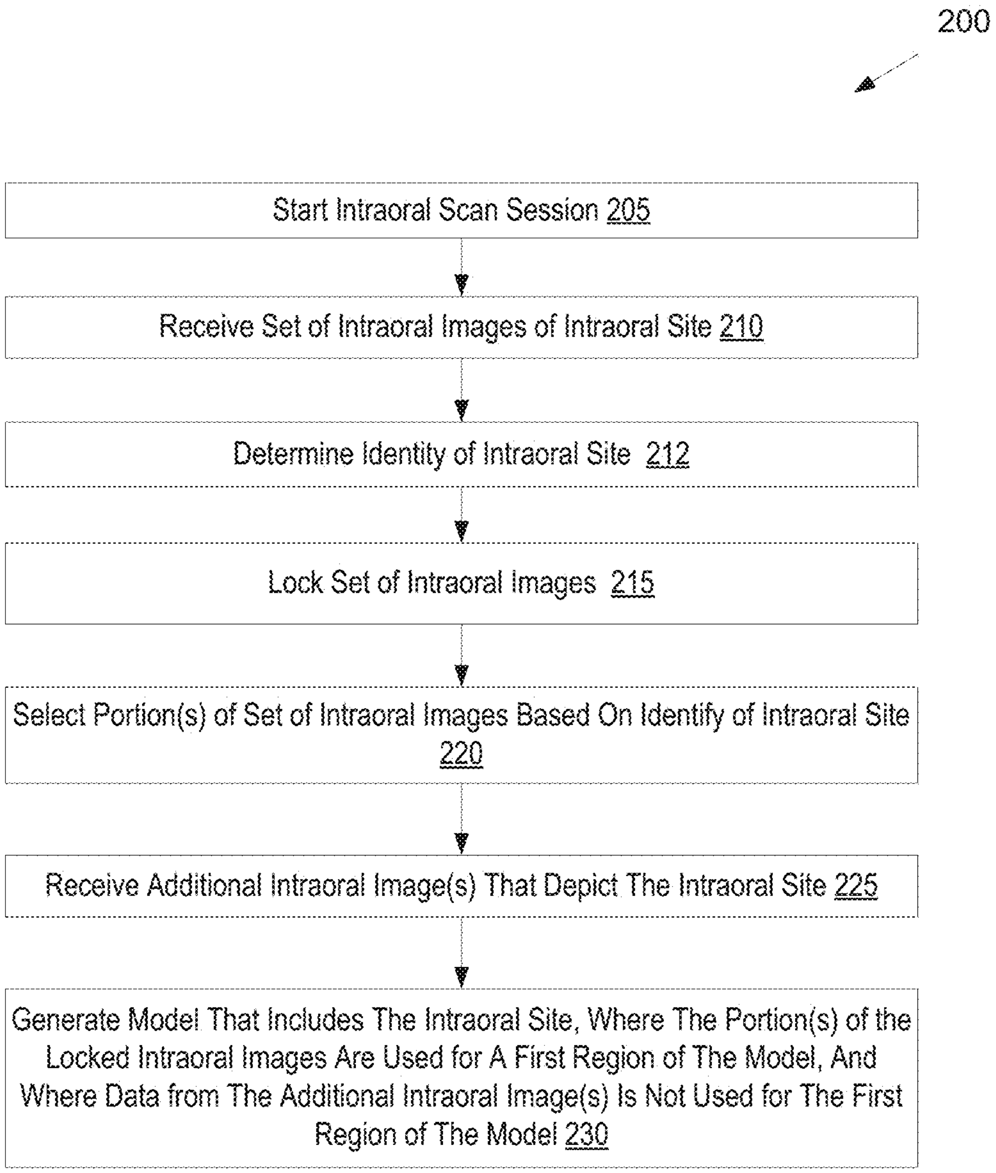
FIG. 2 illustrates a flow diagram for a method of automatically locking an image set of an intraoral site, in accordance with embodiments of the present invention.

FIG. 2 illustrates a flow diagram for a method 200 of automatically locking an image set of an intraoral site, in accordance with embodiments of the present invention. At block 205 of method 200 an intraoral scan session is started. During the intraoral scan session, a dental practitioner uses an intraoral scanner to create a set of intraoral images focused on a particular intraoral site (e.g., focused on a particular tooth). Processing logic may direct the dental practitioner as to which intraoral site (e.g., which tooth) is to be scanned or the dental practitioner may indicate which intraoral site is to be scanned or has been scanned. Alternatively, processing logic may automatically (e.g., algorithmically) identify the intraoral site based on data from the set of intraoral images and/or based on one or more additional sets of intraoral images (e.g., that focus on other intraoral sites). At block 210, processing logic receives a set of intraoral images of the intraoral site. At block 215, processing logic locks the intraoral image data set. This ensures that portions of the intraoral image data set that depict particular areas of the intraoral site (e.g., that depict a particular preparation tooth, including its margin line) will not later be modified or degraded by additional intraoral images.

Figure 7A:
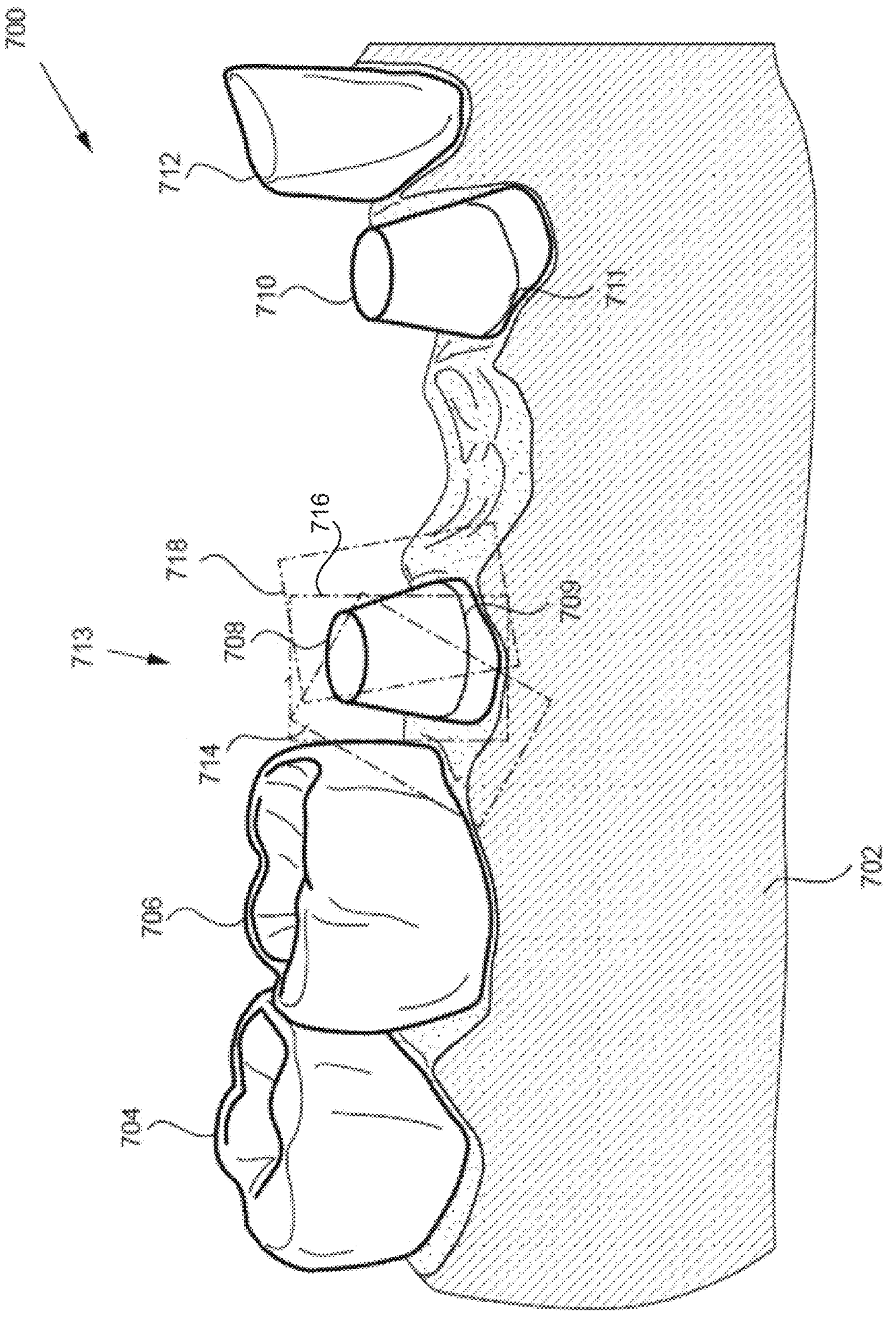
FIG. 7A illustrates a portion of an example dental arch during an intraoral scan session after a first set of intraoral images of a preparation tooth have been generated.

Referring to FIG. 7A, a portion of an example dental arch 700 is illustrated during an intraoral scan session. The dental arch includes two preparation teeth 708, 710 and adjacent teeth 704, 706, 712 as well as a patient's gums 702. As shown, preparation teeth 708, 710 have been ground down to stumps so as to act as abutments and receive a bridge. Preparation tooth 708 includes a finish line 709 and preparation tooth 710 includes a finish line 711. The illustrated finish lines 709, 711 are above the gum line to improve visibility for this example. However, in many instances the finish lines are below the gum line. In one example, cord may have been packed between the preparation tooth 708 and surrounding gums and then removed to cause the finish line 709 to be briefly exposed for scanning.

An intraoral image data set 713 including intraoral image 714, intraoral image 716 and intraoral image 718 is shown. Each of the intraoral images 714-718 may have been generated by an intraoral scanner having a particular distance from the dental surface being imaged. At the particular distance, the intraoral images 714-718 have a particular scan area and scan depth. The shape and size of the scan area will generally depend on the scanner, and is herein represented by a rectangle. Each image may have its own reference coordinate system and origin. Each intraoral image may be generated by a scanner at a particular position (scanning station). The location and orientation of scanning stations may be selected such that together the intraoral images adequately cover an entire target zone. Preferably, scanning stations are selected such that there is overlap between the intraoral images 714-718 as shown. Typically, the selected scanning stations will differ when different scanners are used for the same target area, depending on the capture characteristics of the scanner used. Thus, a scanner capable of scanning a larger dental area with each scan (e.g., having a larger field of view) will use fewer scanning stations than a scanner that is only capable of capturing 3D data of a relatively smaller dental surface. Similarly, the number and disposition of scanning stations for a scanner having a rectangular scanning grid (and thus providing projected scanning areas in the form of corresponding rectangles) will typically be different from those for a scanner having a circular or triangular scanning grid (which would provide projected scanning areas in the form of corresponding circles or triangles, respectively). The intraoral image data set 713 is locked automatically, and may be assigned to a first layer.

Referring back to FIG. 2, at block 220 of method 200 portions of the first set of intraoral images are selected algorithmically by processing logic. The selected portions may correspond to a contour of a tooth or other feature of the intraoral site. The selected portions may be determined based on performing image analysis and applying object recognition techniques, such as edge detection, edge matching, greyscale matching, gradient matching, bag of words models, and so on. Reference data may be used to train processing logic to detect particular objects such as teeth. In one embodiment, the known identity of the tooth or intraoral site is used to assist the object detection process and to select the portions of the intraoral images.

For example, in the example intraoral image data set 713 of FIG. 7A, a contour of the preparation tooth 708 may be generated. All portions of the intraoral images 714-718 of the intraoral image data set 713 that are inside of the contour may be secured from further alteration. In one embodiment, the locked image data set is updated so that the area inside of the contour is locked in the image data set and the area outside of the contour is unlocked.

At block 225 of method 200, processing logic receives one or more additional intraoral images that depict the intraoral site (e.g., that depict a tooth that was the focus of the locked set of intraoral images). These additional intraoral images may be part of one or more additional intraoral image data sets for one or more additional teeth, for example. At block 230, processing logic generates a virtual 3D model that includes the intraoral site. The selected portions of the locked intraoral image (e.g., that are inside of the determined contour) are used to create a first region of the model. For example, the selected portions may be used to create a particular preparation tooth in the 3D model. Data from the additional intraoral images are not used to create the region of the 3D model.

Figure 7B:
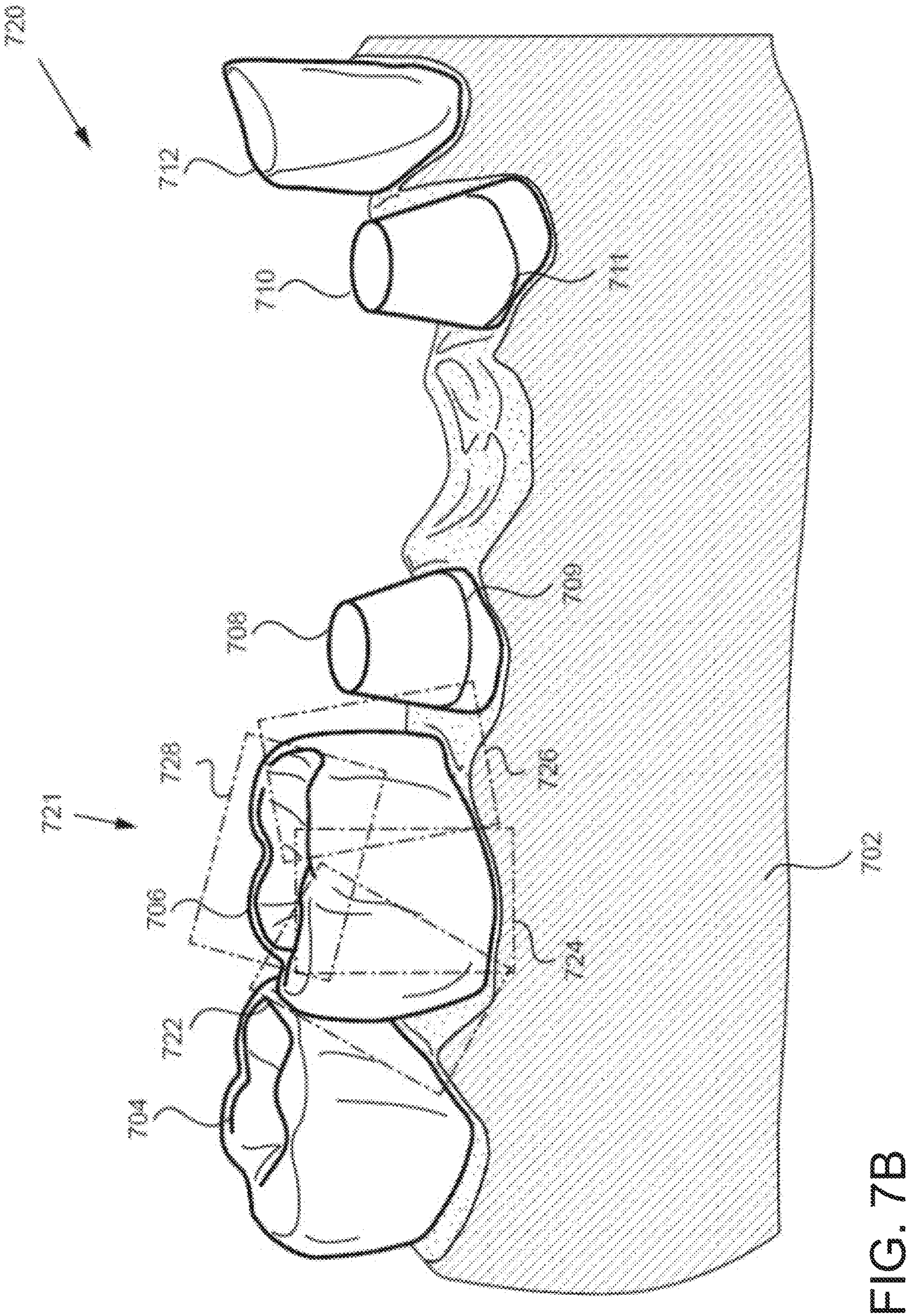
FIG. 7B illustrates the example dental arch of FIG. 7A during the intraoral scan session after a second set of intraoral images of a tooth adjacent to the preparation tooth have been generated.

Referring now to FIG. 7B, the example dental arch of FIG. 7A during the intraoral scan session is shown after a second intraoral image data set 721 has been generated for a tooth 706 adjacent to the preparation tooth 708. Intraoral image data set 721 includes intraoral images 722-728, which focus on adjacent tooth 706. However, as illustrated an area of intraoral image 726 in the second intraoral image data set 721 also depicts preparation tooth 708 and finish line 709. However, since the first intraoral image data set 713 has been locked, data from the second intraoral image data set 721 will not be used when creating a virtual representation of preparation tooth 708 in a 3D model.

Figure 3:
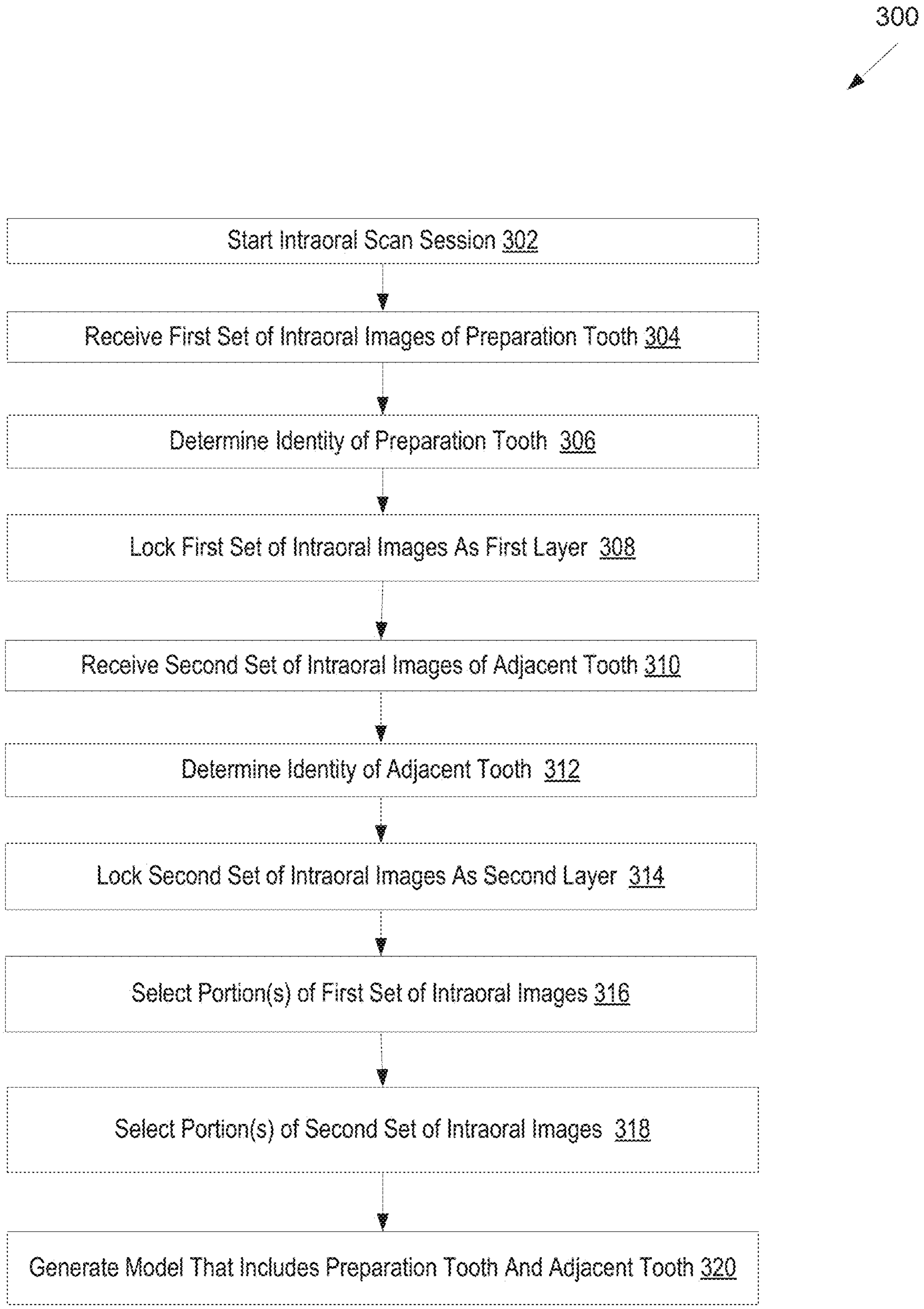
FIG. 3 illustrates a flow diagram for a method of locking multiple image sets of one or more intraoral sites, in accordance with embodiments of the present invention.

FIG. 3 illustrates a flow diagram for a method 300 of locking multiple image sets of one or more intraoral sites, in accordance with embodiments of the present invention. At block 302 of method 300 processing logic starts an intraoral scan session. At block 304, processing logic receives a first set of intraoral images of a preparation tooth. At block 306, processing logic determines an identity of the preparation tooth. At block 308, processing logic locks the first set of intraoral images as a first layer.

At block 310, processing logic receives a second set of intraoral images of another tooth that is adjacent to the preparation tooth. The adjacent tooth may or may not be another preparation tooth. At block 312, processing logic determines an identity of the adjacent tooth. At block 314, processing logic locks the second set of intraoral images as a second layer.

At block 316, processing logic selects portions of the first set of intraoral images. This selection may be made based at least in part on the identity of the preparation tooth. Selecting the portions may include contouring the preparation tooth in the first set of intraoral images and selecting those portions that are within the contour. At block 318, processing logic selects portions of the second set of intraoral images. This selection may be made based at least in part on the identity of the adjacent tooth. Selecting the portions may include contouring the adjacent tooth in the second set of intraoral images and selecting those portions that are within the contour.

At block 320, processing logic generates a virtual 3D model of an intraoral site that includes the preparation tooth, the adjacent tooth and surrounding tissue.

Referring back to FIGS. 7A-7B, intraoral image data set 713 may correspond to the first set of intraoral images of the preparation tooth in method 300. Similarly, intraoral image data set 721 may correspond to the second set of intraoral images of the adjacent tooth in method 300. Accordingly, those portions of intraoral image data set 713 that depict adjacent tooth 706 would not be used to recreate the adjacent tooth in the 3D model and those portions of intraoral image data set 721 that depict preparation tooth 708 would not be used to recreate the preparation tooth in the 3D model.

Figure 4:
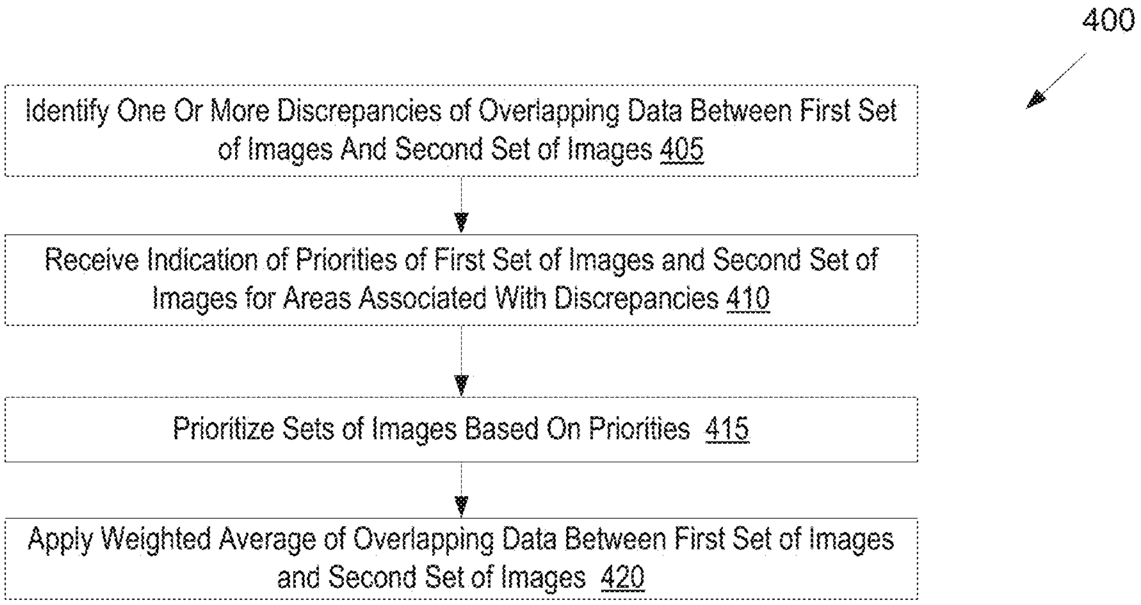
FIG. 4 illustrates a flow diagram for a method of stitching together multiple image sets of one or more intraoral sites, in accordance with embodiments of the present invention.

FIG. 4 illustrates a flow diagram for a method 400 of stitching together multiple image sets of one or more intraoral sites, in accordance with embodiments of the present invention. Processing logic may receive a first set if intraoral images (e.g., that focus on a preparation tooth) and a second set of intraoral images (e.g., that focus on an adjacent tooth or a full or partial arch). At block 405 of method 400, processing logic identifies one or more discrepancies of overlapping data between the first set of intraoral images and the second set of intraoral images. For example, the first set of intraoral images and second set of intraoral images may each depict the gums between the preparation tooth and the adjacent tooth. However, the depictions of the gums in these intraoral image data sets may not line up perfectly. For example, blood and/or saliva may have accumulated on the gums between generation of the first intraoral image data set and the second intraoral image data set, or the positioning of the gums may be slightly different in the two intraoral image data sets. To create a 3D model that includes both the preparation tooth and the adjacent tooth, the data from the two intraoral image data sets should be merged, and the conflicts in the data remedied.

At block 410, processing logic receives an indication of priorities of the first set of images and the second set of images. For example, the first set of images may be known to have a higher quality or be more important, and so a higher priority may be assigned to the first set of images. At block 415, processing logic uses the received indications of priority to prioritize the image data sets. At block 420, processing logic applies a weighted average of the overlapping data between the first set of images and the second set of images to merge the overlapping data. The weights that are applied to the image data sets may be based on their priority. For example, the first image data set assigned the higher priority may be assigned a weight of 70% and the second set of intraoral images may be assigned a weight of 30%. Thus, when the data is averaged, the merged result will look more like the depiction from the first image data set and less like the depiction from the second image data set.

In one embodiment, processing logic may render different versions of the 3D model, each version showing a different prioritization and/or different weightings of the intraoral image data sets. The user may visually inspect the different renderings and select which rendering looks the most accurate. Processing logic may then prioritize the image data sets accordingly and then apply the appropriate weighted average associated with the user selection to create the 3D model.

Figure 5:
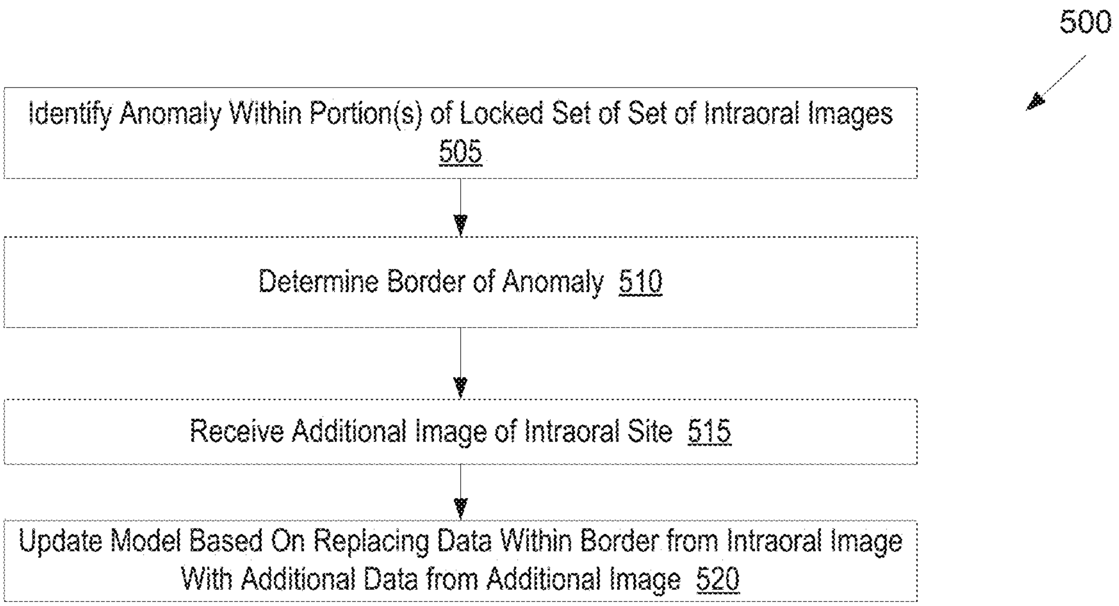
FIG. 5 illustrates a flow diagram for a method of detecting an anomaly in an image set of an intraoral site and replacing the anomaly with data from an additional intraoral image, in accordance with embodiments of the present invention.

FIG. 5 illustrates a flow diagram for a method 500 of correcting an anomaly in an intraoral image data set and/or in a 3D virtual model generated from such an intraoral image data set, in accordance with embodiments of the present invention. The intraoral image data set may be a set of discrete images (e.g., taken from a point-and-shoot mode) or multiple frames of an intraoral video (e.g., taken in a continuous scanning or video mode). The intraoral image data set may have been for a particular dental site (e.g., tooth) of a patient, and may be locked to preserve the intraoral image data set.

At block 505 of method 500, processing logic identifies an anomaly within the locked set of intraoral images and/or in a 3D model generated from the locked set of intraoral images. The anomaly may be identified by performing image processing on the intraoral image data set and applying a set of criteria thereto. In one embodiment, processing logic determines if any voxels or sets of voxels in the intraoral images or 3D model satisfy the one or more criteria. Different criteria may be used to identify different classes of anomalies. In one embodiment, missing image data is used to identify anomalies that might be voids. For example, voxels at areas that were not captured by the intraoral images may be identified.

At block 510, processing logic determines a border of the anomaly, such as by generating a contour of the anomaly. In one embodiment, processing logic interpolates a shape for the anomaly based on geometric features surrounding the anomaly and/or based on geometric features of the anomaly (if such features exist). For example, if the anomaly is a void, then the regions around the void may be used to interpolate a surface shape of the void. The shape of the anomaly may then be used to create the contour. All data outside of the contour may remain locked and unchangeable, while data inside of the contour may be replaced with data from new intraoral images.

Processing logic may provide an indication of the anomaly via a user interface. The contour of the anomaly may be displayed in manner to contrast the anomaly from surrounding imagery. For example, teeth may be shown in white, while the anomaly may be shown in red, black, blue, green, or another color. Additionally or alternatively, an indicator such as a flag may be used as an indication of the anomaly. The indicator may be remote from the anomaly but include a pointer to the anomaly. The anomaly may be hidden or occluded in many views of the intraoral site. However, the indicator may be visible in all or many such views.

Figure 7D:
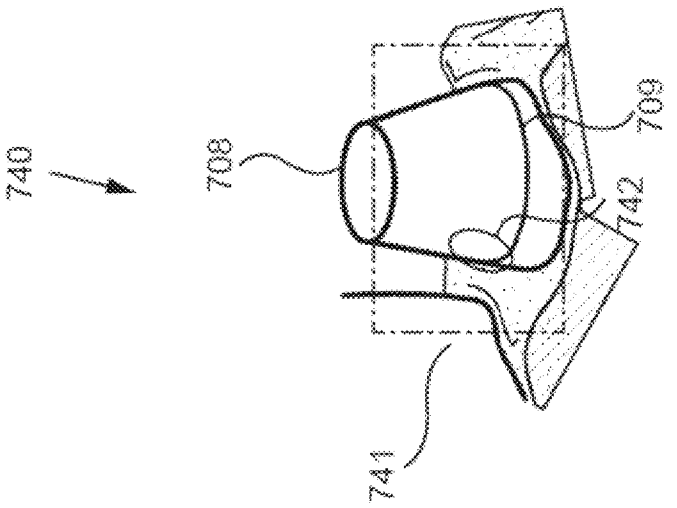
FIG. 7D illustrates a model created from the first set of intraoral images of FIG. 7C with data from an additional intraoral image.
Figure 7C:
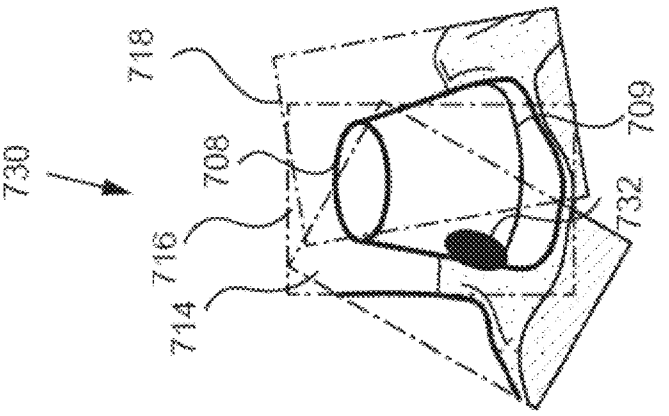
FIG. 7C illustrates the first set of intraoral images of FIG. 7A, wherein the first set of intraoral images includes an anomaly.

Referring to FIG. 7C, a set of intraoral images 730 is shown that includes a preparation tooth 708 having a finish line 709 and an anomaly 732. As shown, the anomaly 732 has been contoured and has a particular shape (of an oval in this instance). The set of intraoral images 730 includes intraoral images 714-718.

Referring back to FIG. 5, at block 515, processing logic receives an additional image of the intraoral site. The additional image may include data for the region of the 3D model or initial set of intraoral images where the anomaly was detected. At block 520, processing logic updates the virtual 3D model based on replacing the data of the original set of intraoral images within the border or contour with additional data from the additional image of the intraoral site. Thus, the anomaly may be corrected without affecting a remainder of the virtual 3D model.

Referring FIG. 7D, a virtual 3D model 740 created from the set of intraoral images 730 and data from an additional intraoral image 709 is shown. The rendering of the preparation tooth 708 outside of the contour of the anomaly 742 is unaffected by image data from the additional intraoral image 741. However, the portion of the preparation tooth 708 that is inside the contour of the anomaly 742 is rendered based on data from the additional intraoral image 709.

Figure 6:
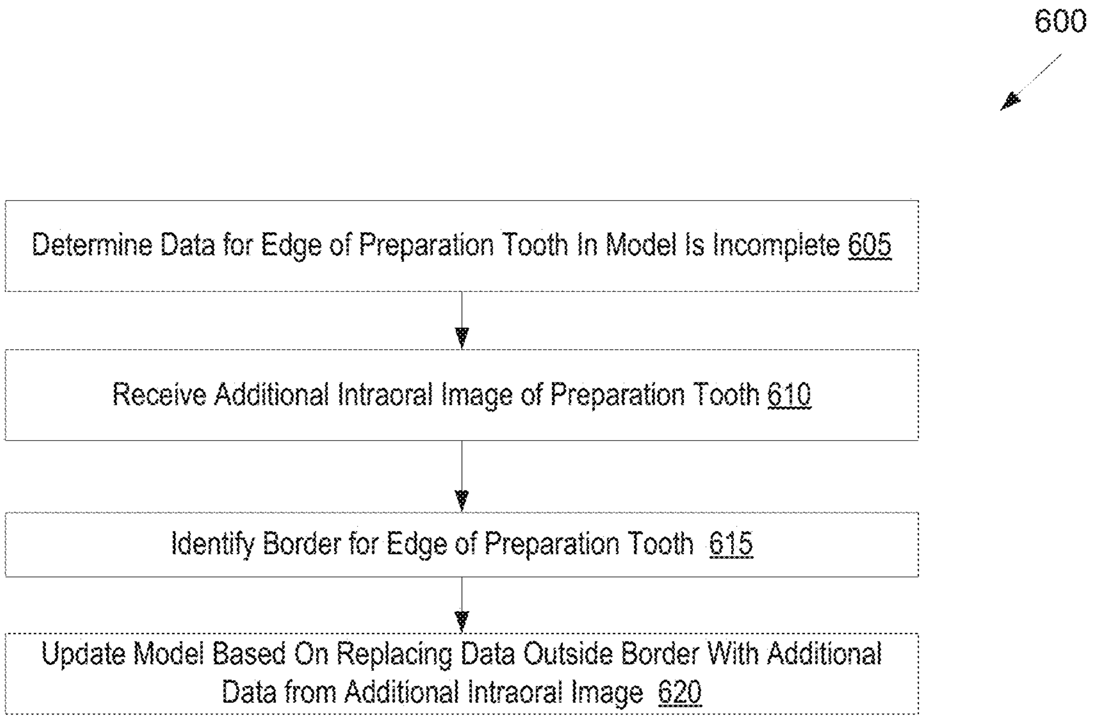
FIG. 6 illustrates a flow diagram for a method of extending a model of an intraoral site where an incomplete edge is detected, in accordance with embodiments of the present invention.

FIG. 6 illustrates a flow diagram for a method 600 of extending a model of an intraoral site where an incomplete tooth or other object is detected, in accordance with embodiments of the present invention. At block 605 of method 600, processing logic determines that data for a preparation tooth (or other intraoral site) in a 3D model is incomplete. For example, processing logic may determine that an edge of the preparation tooth has been cut off. This determination may be made, for example, based on comparing an expected contour of the preparation tooth or other tooth with a contour of the preparation tooth or other tooth in a computed 3D model. If the computed contour varies from the expected contour by more than a threshold amount, processing logic may determine that the preparation tooth or other tooth is cut off in the model. In one embodiment, such a determination is made responsive to a user indication that the preparation tooth or other tooth in the 3D model is incomplete. For example, a user may review the 3D model, determine that a portion of a tooth is cut off, and manually enter an expansion mode to add data for the area that was cut off. Alternatively, such a determination may be made algorithmically without first receiving user input (e.g., based on performing image processing).

Figure 7E:
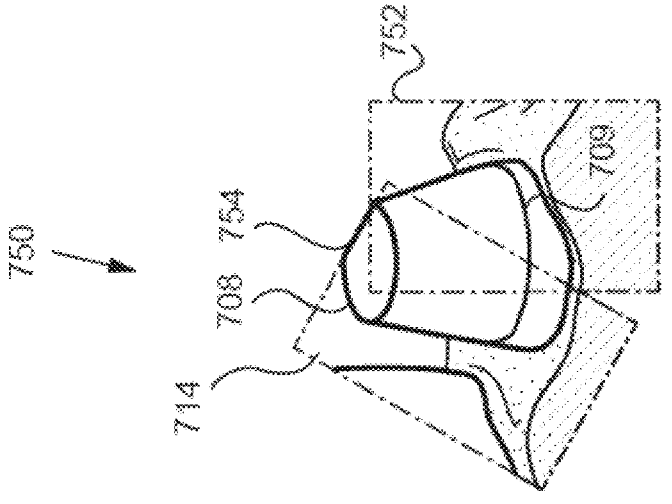
FIG. 7E illustrates a set intraoral images of a preparation tooth, wherein the set of intraoral images fails to capture all of the preparation tooth.

Referring to FIG. 7E, a set of intraoral images 750 includes intraoral images 714 and 752. The set of intraoral images 750 depicts a preparation tooth 708 having a finish line 709. However, an edge 754 of the preparation tooth 708 is cut off.

At block 610, processing logic receives an additional intraoral image of the preparation tooth (or other tooth). At block 615, processing logic may identify a border for the edge of the preparation tooth. In one embodiment, this includes generating a contour of the edge of the preparation tooth at the border. In some instances this may already have been performed at block 605. The shape of the edge may be used to create the contour or border. All data inside of the contour may remain locked and unchangeable.

At block 620, processing logic updates the model based on replacing data outside the border with additional data from the additional intraoral image. Processing logic determines what portion of the additional intraoral image of the preparation tooth depicts the portion of the preparation tooth that was cut off in the initial set of intraoral images (e.g., outside the border of the edge where data was cut off). The identified portion of the additional intraoral image may then be appended to the initial set of intraoral image and used to extend the preparation tooth (or other tooth) in the model.

Figure 7F:
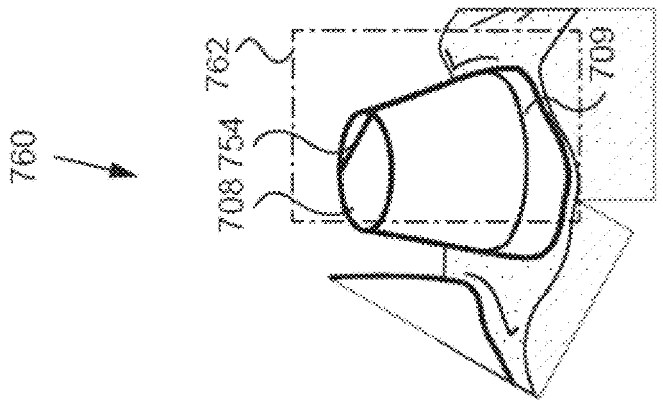
FIG. 7F illustrates a model created from the first set of intraoral images of FIG. 7E with data from an additional intraoral image.

Referring to FIG. 7F, a virtual 3D model 760 created from the set of intraoral images 750 of FIG. 7E with data from an additional intraoral image 762 is shown. The rendering of the preparation tooth 708 inside of a contour of the preparation tooth 708 is unaffected by image data from the additional intraoral image 762. However, a portion of the intraoral image 762 showing the cut off region outside of the edge 754 is used to extend the preparation tooth 708 in the 3D model 760.

Figure 8:
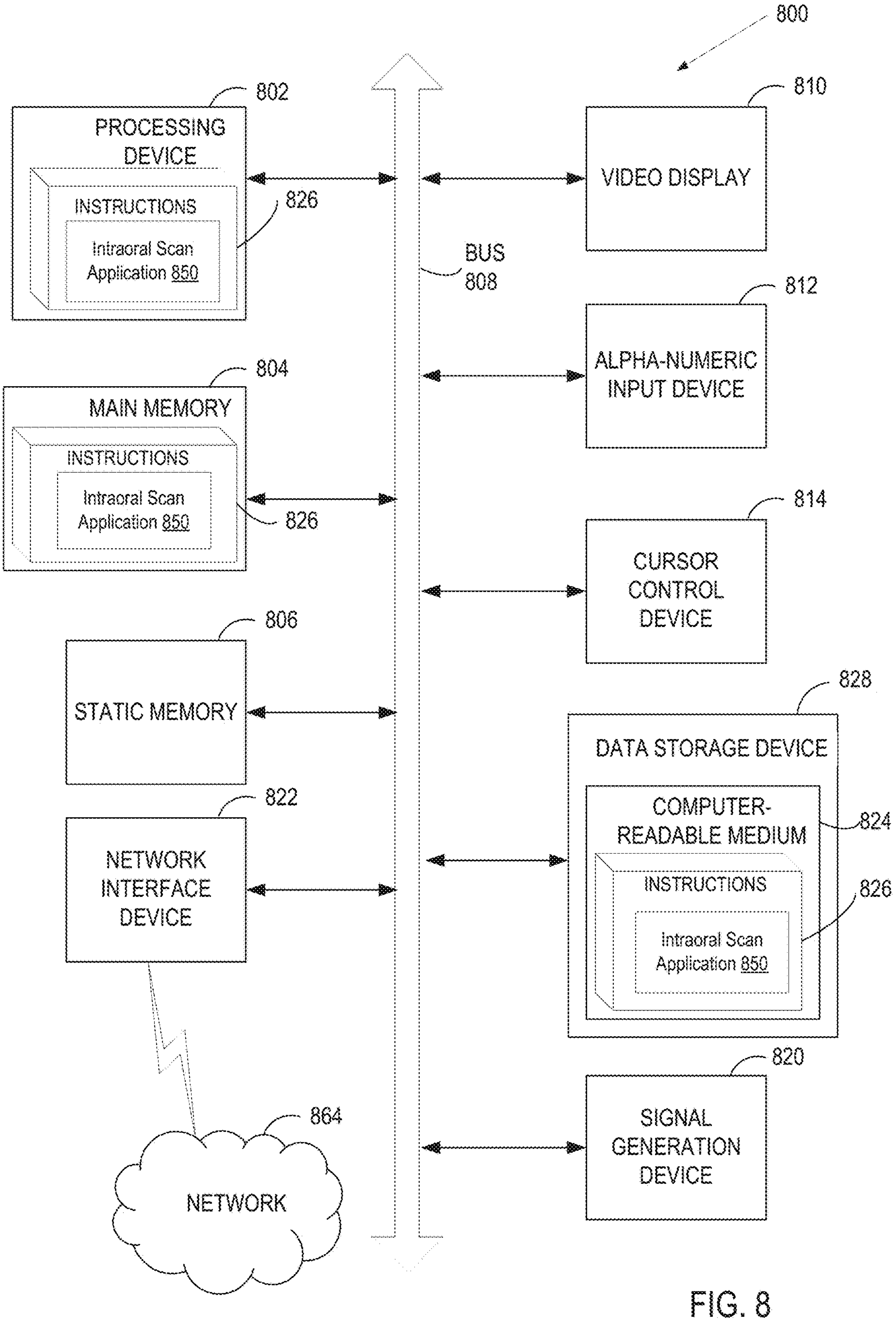
FIG. 8 illustrates a block diagram of an example computing device, in accordance with embodiments of the present invention.

FIG. 8 illustrates a diagrammatic representation of a machine in the example form of a computing device 800 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. The term machine shall also refer to an integrated all-in-one device that includes an intraoral scanner and a computing device (e.g., scanner 150 and computing device 105 of FIG. 1).

The example computing device 800 includes a processing device 802, a main memory 804 (e.g., read-only memory (ROM), flash memory, dynamic random access memory (DRAM) such as synchronous DRAM (SDRAM), etc.), a static memory 806 (e.g., flash memory, static random access memory (SRAM), etc.), and a secondary memory (e.g., a data storage device 828), which communicate with each other via a bus 808.

Processing device 802 represents one or more general-purpose processors such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 802 may also be one or more special-purpose processing devices such as an application specific integrated circuit (ASIC), a field programmable gate array (FPGA), a digital signal processor (DSP), network processor, or the like. Processing device 802 is configured to execute the processing logic (instructions 826) for performing operations and steps discussed herein.

The computing device 800 may further include a network interface device 822 for communicating with a network 864. The computing device 800 also may include a video display unit 810 (e.g., a liquid crystal display (LCD) or a cathode ray tube (CRT)), an alphanumeric input device 812 (e.g., a keyboard), a cursor control device 814 (e.g., a mouse), and a signal generation device 820 (e.g., a speaker).

The data storage device 828 may include a machine-readable storage medium (or more specifically a non-transitory computer-readable storage medium) 824 on which is stored one or more sets of instructions 826 embodying any one or more of the methodologies or functions described herein. A non-transitory storage medium refers to a storage medium other than a carrier wave. The instructions 826 may also reside, completely or at least partially, within the main memory 804 and/or within the processing device 802 during execution thereof by the computer device 800, the main memory 804 and the processing device 802 also constituting computer-readable storage media.

The computer-readable storage medium 824 may also be used to store an intraoral scan application 850, which may correspond to the similarly named component of FIG. 1. The computer readable storage medium 824 may also store a software library containing methods for an intraoral scan application 850. While the computer-readable storage medium 824 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium other than a carrier wave that is capable of storing or encoding a set of instructions for execution by the machine and that cause the machine to perform any one or more of the methodologies of the present invention. The term "computer-readable storage medium" shall accordingly be taken to include, but not be limited to, solid-state memories, and optical and magnetic media.

It is to be understood that the above description is intended to be illustrative, and not restrictive. Many other embodiments will be apparent upon reading and understanding the above description. Although embodiments of the present invention have been described with reference to specific example embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. The scope of the invention should, therefore, be determined with reference to the appended claims, along with the full scope of equivalents to which such claims are entitled.

What is claimed is:

1. A system, comprising:

an intraoral scanner to generate a plurality of intraoral images of one or more dental sites; and one or more computing devices configured to:

receive an intraoral image comprising a depiction of a first tooth;

determine a contour of the first tooth in the intraoral image;

select a portion of the intraoral image that is within the contour of the first tooth;

lock the portion of the intraoral image that is within the contour of the first tooth to prevent data for the portion of the intraoral image from being modified by data from other intraoral images; and generate a 3D model comprising the first tooth and one or more other intraoral objects based at least in part on the intraoral image and one or more additional intraoral images, wherein the locked portion of the intraoral image is used for the first tooth in the 3D model, and wherein, due to the portion of the intraoral image being locked, data from the one or more additional intraoral images that also depict a portion of the first tooth is used for the one or more other intraoral objects in the 3D model but is not used for the first tooth in the 3D model to prevent the data for the portion of the intraoral image from being modified.

2. The system of claim 1, wherein the one or more computing devices are further configured to perform image processing on the intraoral image to determine the contour of the first tooth.

3. The system of claim 1, wherein the one or more computing devices are further configured to:

determine an identity of the first tooth;

wherein the portion of the intraoral image is selected based at least in part on the identity of the first tooth.

4. The system of claim 1, wherein the intraoral image is a member of a first set of intraoral images of the plurality of intraoral images, wherein the one or more additional intraoral images are members of a second set of intraoral images, and wherein the one or more computing devices are further configured to:

for each intraoral image that is a member of the first set of intraoral images, select a portion of that intraoral image depicting the portion of the first tooth; and lock at least the portion of the first set of intraoral images.

5. The system of claim 4, wherein the one or more computing devices are further configured to:

receive the second set of intraoral images, wherein the second set of intraoral images is of the one or more other intraoral objects, and wherein one or more portions of the second set of intraoral images also depict the first tooth; and disregard the one or more portions of the second set of intraoral images when generating the 3D model, wherein the second set of intraoral images does not alter or add noise to a representation of the first tooth in the 3D model as a result of the first set of intraoral images being locked.

6. The system of claim 4, wherein the one or more computing devices are further configured to:

stitch the first set of intraoral images to the second set of intraoral images, the stitching comprising:

identifying one or more discrepancies of overlapping data between the first set of intraoral images and the second set of intraoral images;

prioritizing the first set of intraoral images over the second set of intraoral images; and applying a weighted average of the overlapping data between the first set of intraoral images and the second set of intraoral images, wherein data from the first set of intraoral images has a higher weight than data from the second set of intraoral images.

7. The system of claim 4, wherein one or more portions of the second set of intraoral images that are inside of the contour are not applied for the 3D model, and wherein one or more additional portions of the second set of intraoral images that are outside of the contour are applied for the 3D model.

8. The system of claim 1, wherein the one or more computing devices are further configured to:

identify an anomaly;

determine a border of the anomaly;

receive an additional intraoral image; and update the 3D model based on replacing data within the border with additional data from the additional image.

9. The system of claim 8, wherein the anomaly comprises at least one of a void, noise, or unrealistic data.

10. The system of claim 1, wherein the portion of the first tooth comprises a portion of a preparation.

11. The system of claim 1, wherein the one or more computing devices are further configured to:

determine that data for the first tooth is incomplete;

receive an additional intraoral image of the first tooth;

identify a border for an edge of the first tooth where the data for the first tooth is incomplete; and update the 3D model based on replacing data outside the border with additional data from the additional intraoral image to expand the 3D model at the edge.

12. The system of claim 1, wherein selecting the portion of the intraoral image comprises algorithmically selecting the portion based at least in part on an identity of the first tooth and using (a) stored information about the first tooth and (b) analysis of image data from the intraoral image.

13. A non-transitory storage medium having instructions that, when executed by one or more processing devices, cause the one or more processing devices to perform operations comprising:

receiving a first intraoral image data set associated with a first tooth;

determining a contour of the first tooth in the first intraoral image data set;

locking portions of intraoral images in the first intraoral image data set that are within the contour of the first tooth;

receiving a second intraoral image data set associated with one or more other intraoral objects, wherein one or more intraoral images in the second intraoral image data set depict the first tooth; and generating a 3D model comprising the first tooth and the one or more other intraoral objects based on the first intraoral image data set and the second intraoral image data set, wherein generating the 3D model comprises combining data from the intraoral images of the first intraoral image data set and data from the intraoral images of the second intraoral image data set;

wherein the locked portions of the intraoral images in the first intraoral image data set are used for a first region of the 3D model associated with the first tooth, and wherein data from the second intraoral image data set that also depicts the first tooth is not used for the first region of the 3D model.

14. The non-transitory storage medium of claim 13, wherein the second intraoral image data set is used for one or more additional regions of the 3D model associated with the one or more other intraoral objects.

15. The non-transitory storage medium of claim 13, wherein the first tooth comprises a preparation.

16. The non-transitory storage medium of claim 13, the operations further comprising:

performing image processing on the first intraoral image data set to determine the contour of the first tooth.

17. The non-transitory storage medium of claim 13, the operations further comprising:

determining an identity of the first tooth in the first intraoral image data set;

wherein a portion of the first intraoral image data set that is within the contour of the first tooth is selected based at least in part on the identity of the first tooth.

18. The non-transitory storage medium of claim 13, the operations further comprising:

determining that the first tooth is a first preparation tooth;

wherein a portion of the first intraoral image data set that is within the contour of the first tooth is selected based at least in part responsive to determining that the first tooth is the first preparation tooth.

19. The non-transitory storage medium of claim 18, wherein the contour of the first tooth is a contour of a margin line of the first preparation tooth.

20. The non-transitory storage medium of claim 13, wherein generating the 3D model comprises:

stitching the first intraoral image data set to the second intraoral image data set, the stitching comprising:

identifying one or more discrepancies of overlapping data between the first intraoral image data set and the second intraoral image data set;

prioritizing a first one of the first intraoral image data set and the second intraoral image data set over a second one of the first intraoral image data set and the second intraoral image data set; and applying a weighted average of the overlapping data between the first intraoral image data set and the second intraoral image data set in accordance with the prioritizing.

* * * * *